US008419665B2

(12) United States Patent
Cook

(10) Patent No.: US 8,419,665 B2
(45) Date of Patent: Apr. 16, 2013

(54) VARIABLE LENGTH CALF WRAP FOR IMPULSE THERAPY

(75) Inventor: Gordon John Cook, Andover (GB)

(73) Assignee: Covidien LP, Mansfield, MA (US)

( * ) Notice: Subject to any disclaimer, the term of this patent is extended or adjusted under 35 U.S.C. 154(b) by 743 days.

(21) Appl. No.: 12/448,799

(22) PCT Filed: Jan. 9, 2008

(86) PCT No.: PCT/GB2008/000066
§ 371 (c)(1),
(2), (4) Date: Jul. 8, 2009

(87) PCT Pub. No.: WO2008/084225
PCT Pub. Date: Jul. 17, 2008

(65) Prior Publication Data

US 2011/0004132 A1 Jan. 6, 2011

(30) Foreign Application Priority Data

Jan. 10, 2007 (GB) .................................. 0700436.9

(51) Int. Cl.

| | |
|---|---|
| *A61H 7/00* | (2006.01) |
| *A61H 19/00* | (2006.01) |
| *A61F 5/00* | (2006.01) |
| *A61F 13/06* | (2006.01) |
| *A61F 13/00* | (2006.01) |
| *A61F 5/37* | (2006.01) |
| *A61L 15/00* | (2006.01) |
| *A61B 19/00* | (2006.01) |

(52) U.S. Cl.
USPC ........... 601/148; 601/149; 601/150; 601/151; 601/152; 601/153; 602/5; 602/13; 602/60; 602/61; 602/62; 602/75; 128/846; 128/869; 128/882

(58) Field of Classification Search .......... 601/148–153; 602/5, 13, 23, 26–27, 60–62, 75; 128/846, 128/869, 882
See application file for complete search history.

(56) References Cited

U.S. PATENT DOCUMENTS 5,014,681 A * 5/1991 Neeman et al. ............... 601/152
2005/0070828 A1* 3/2005 Hampson et al. ............. 601/152

FOREIGN PATENT DOCUMENTS

| | | | |
|---|---|---|---|
| GB | 2 373 444 | A | 9/2002 |
| JP | 2003-310679 | A | 11/2003 |
| WO | WO 2006/033096 | A | 3/2006 |
| WO | WO 2006/064223 | A | 6/2006 |

OTHER PUBLICATIONS

Notice of Rejection dated May 22, 2012 from related Japanese application serial No. 2009-545225, English translation, 2 pages.

* cited by examiner

*Primary Examiner* — Patricia Bianco
*Assistant Examiner* — Brandon L Jackson
(74) *Attorney, Agent, or Firm* — John Paul Mello, Esq.

(57) ABSTRACT

An inflatable garment for applying to parts of the body such as the calf of the leg as a means of enhancing blood circulation in the body. The garment is of universal application in the sense that it comprises two wrap halves (8, 9) provided with inflatable bladders (4, 5, 6). The two wrap halves can be selectively coupled together in such a way as to provide a variable overall length of garment wrap to suit calf's of differing size while at the same time maintaining the integrity of fluid communication between the bladders on the respective wrap halves.

7 Claims, 7 Drawing Sheets

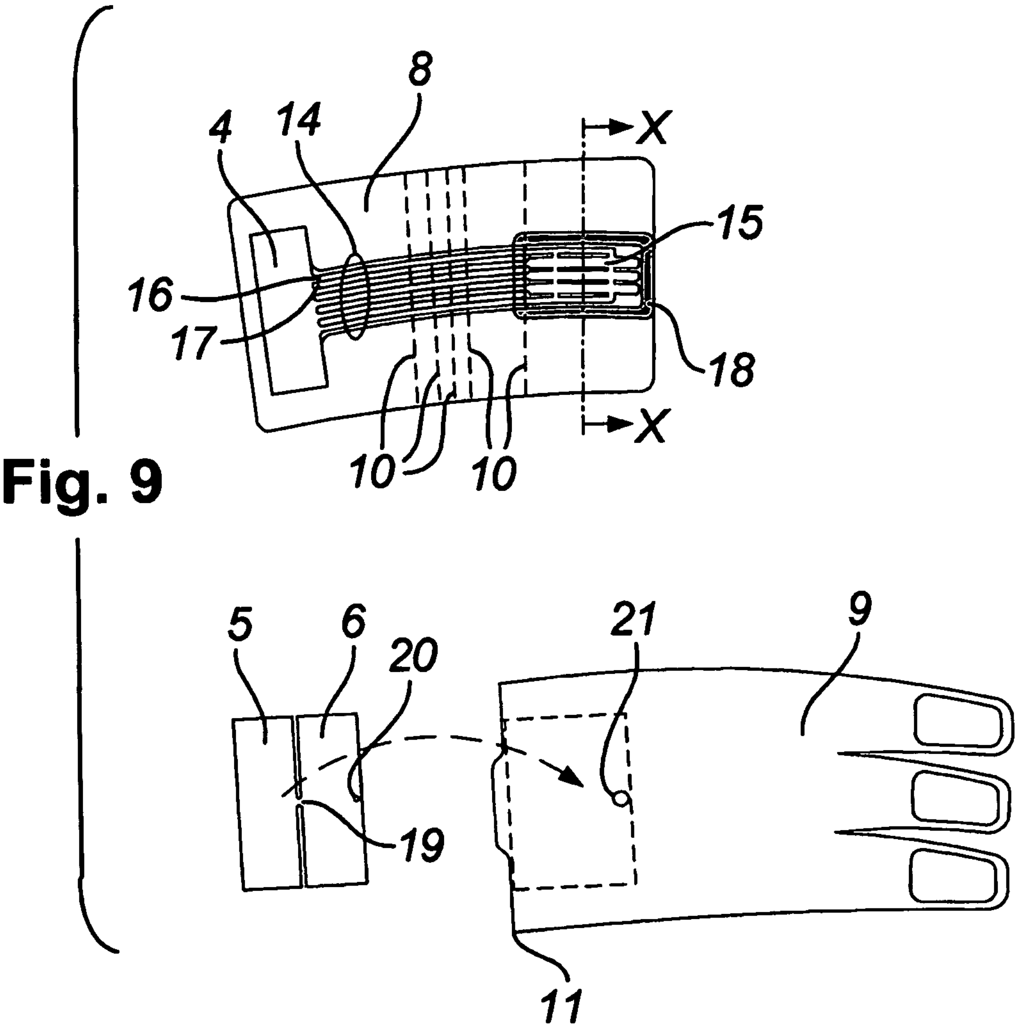
Fig. 9
Fig. 9a
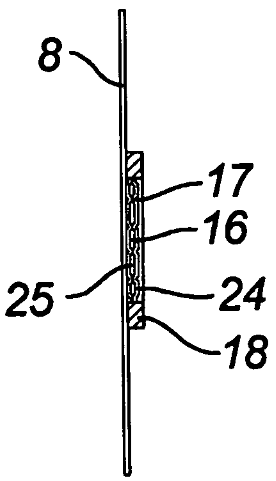

VARIABLE LENGTH CALF WRAP FOR IMPULSE THERAPY

FIELD OF THE INVENTION

The present invention relates to the enhancement of blood circulation in the body and particularly to a device for bringing this about.

BACKGROUND

The use of an inflatable garment applied to the leg as a means of enhancing blood circulation in the body is a well-established technique with proven clinical benefits.

The garment usually comprises an inflatable bladder or bladders contained as part of or integral to a means of attaching or securing the garment around the leg either above or more conveniently below the knee. During use the bladder is filled with a fluid such as air to expand and apply force to the body, directed in such a way as to empty the veins of blood. The bladder is held pressurised for a period before releasing the fluid and then the cycle repeated. The rate of filling or venting of the bladder may vary from fractions of a second to several seconds according to the application.

The garment is attached, for example, to the lower leg normally by wrapping the device around the limb and securing by means of hook and loop closure. For optimal performance the garment is selected from a range of sizes e.g. small, medium or large corresponding to the circumference of the patient's calf or a universal sized garment is indicated with inherent limitations when applied to a diverse anatomical population.

Recent advances in calf impulse therapy have recognised merit in using selectively placed bladder arrangements targeted to correspond with anatomical features of the leg rather than inflating against the calf generally by means of single, dual or preferably triple bladder elements. A distinguishing feature of the prior art is the relevant positioning of a single bladder at the front out-step side of the leg with a dual bladder positioned relatively rearward. The positional separation of the bladder elements is specified according to calf circumference, based upon anatomical data.

As a novel improvement of the prior art, this disclosure reveals how a universal garment may be constructed utilising selectively placed bladders and discloses detail of interconnection between individual bladder components. These improvements are directed to solving the deficiencies and limitations of the prior art.

The methods disclosed are initially configured and illustrated for use in calf impulse technology devices such as used with the A-V Impulse System®. There will be similar applications for this sizing concept in foot and hand impulse technology and other intermittent pneumatic compression devices.

SUMMARY OF THE INVENTION

According to the invention there is provided an inflatable medical garment for applying to parts of the body such as the foot, calf and hand as a means of enhancing blood circulation in the body comprising a circumferential wrap provided with one or more inflatable bladders, means for securing the wrap around the body part such that upon cyclic inflation of the bladders a cyclical pressure is applied to the body part to drive blood around the body and means incorporated in the garment for adjusting the fit of the garment in accordance with body parts of differing shape and size.

Preferred features and advantages of the invention will be explained in greater detail below with reference to the drawings accompanying this disclosure.

BRIEF DESCRIPTION OF THE DRAWINGS

The invention will now be described by way of example with reference to the accompanying drawings wherein:

FIG. 9 is a plan view of a two-piece calf garment including a further preferred method of interconnection between bladder elements;

FIG. 9*a* is an enlarged sectional view of the garment of FIG. 9 along the section X-X;

PREFERRED EMBODIMENTS OF THE INVENTION

In the description which follows, all illustrations are shown for the right leg. It will be understood that garments used on the left leg are a mirror-image thereof.

Figure 1:
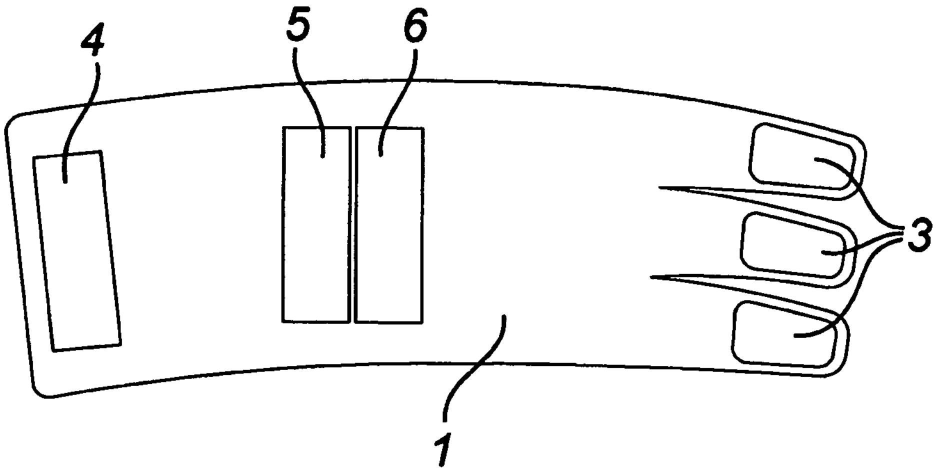
FIG. 1 is the plan view showing a one-piece calf impulse technology garment for mounting around the calf.

The impulse therapy garment shown in FIG. 1 comprises a circumferential wrap 1 configured to anatomically conform to the leg in the region of the calf and be secured around the calf. The garment is secured to a leg by singular or multiple hook closure(s) 3 engaging with loop material being the outside facing of the wrap 1.

The garment incorporates one or more bladders 4, 5, 6 located between the wrap and calf that are rapidly inflated in a fraction of a second to as much as ~200 mmHg, with a fluid such as air, to apply force to the limb and held pressurised for up to 3 seconds before venting. Bladders are typically constructed from 2 layers of thin polymeric film such as PVC, welded by Radio Frequency means around the periphery.

Figure 2:
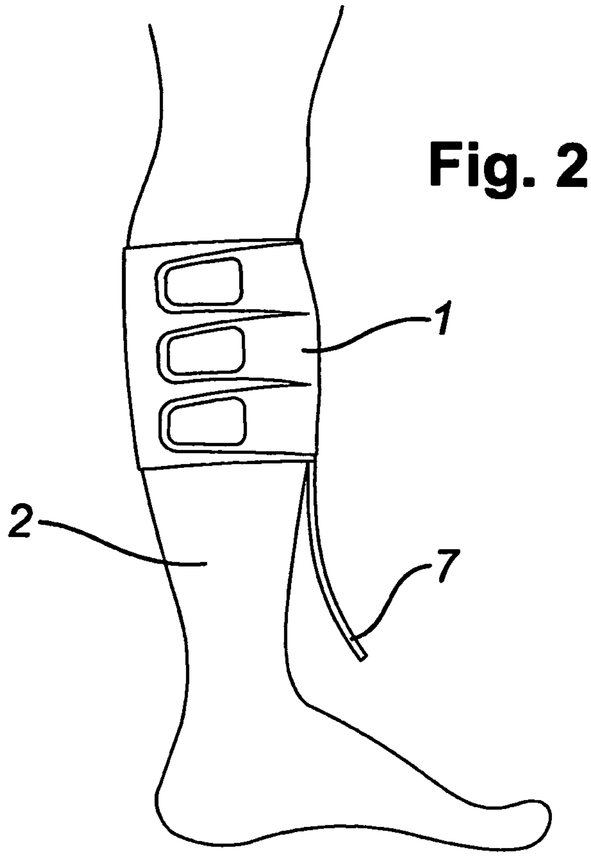
FIG. 2 is a side elevation of the garment illustrated in FIG. 1 applied to the calf of a human leg.

In FIG. 2 the garment of FIG. 1 is shown fitted around the calf of the leg 2. An air connection is made to the garment through hose 7 in order to inflate and deflate the bladders from an external controller.

Figure 3:
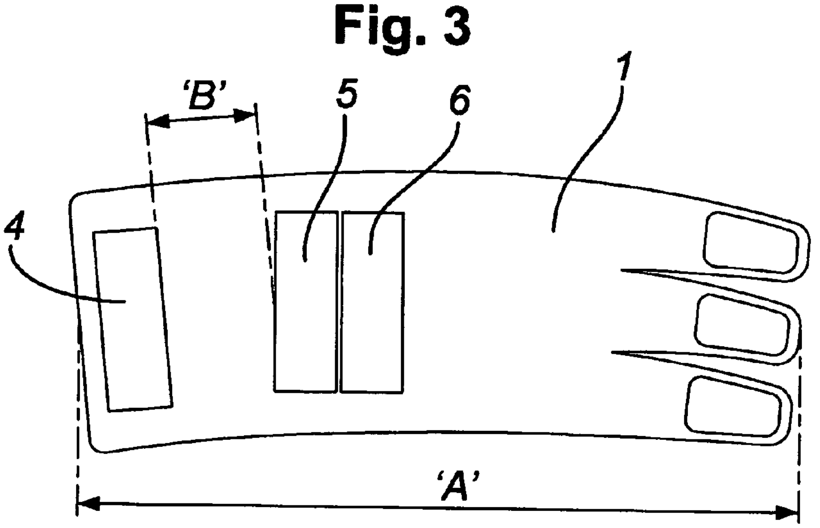
FIG. 3 is a plan view of the calf garment of FIG. 1 for use with a person of small physique.

The garment 1, see FIG. 3, has a dimension 'A' which relates to a calf of minimal circumference as might be evident to a person of smaller physique. In addition, dimension 'B' correspondingly relates to separation of single bladder 4 from dual bladders 5, 6. The example shown is constructed in the form of a one-piece garment where for reference only, dimension 'A' is of the order of 50 cm and dimension 'B' 8 cm.

Figure 4:
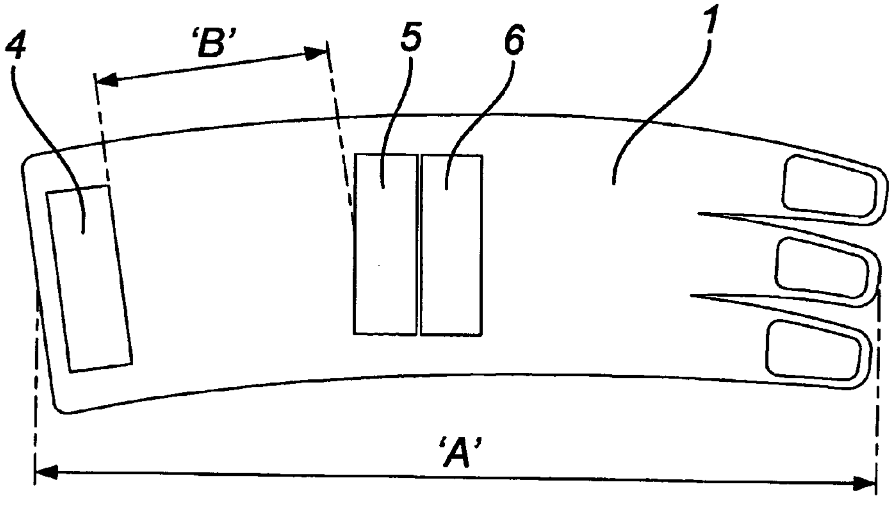
FIG. 4 is a plan view of the calf garment of FIG. 1 for use with a person of larger physique.

The garment 1 shown in FIG. 4 has a dimension 'A' which relates to a calf of maximal circumference as might be evident to a person of larger physique. In addition, dimension 'B' correspondingly relates to separation of single bladder 4 from dual bladders 5, 6 illustrating both a wider garment and with greater separation between bladder components than illustrated in FIG. 3. The example shown is constructed in the form of a one-piece garment where for reference only, dimension 'A' is of the order of 60 cm and dimension 'B' 17 cm.

Figure 5:
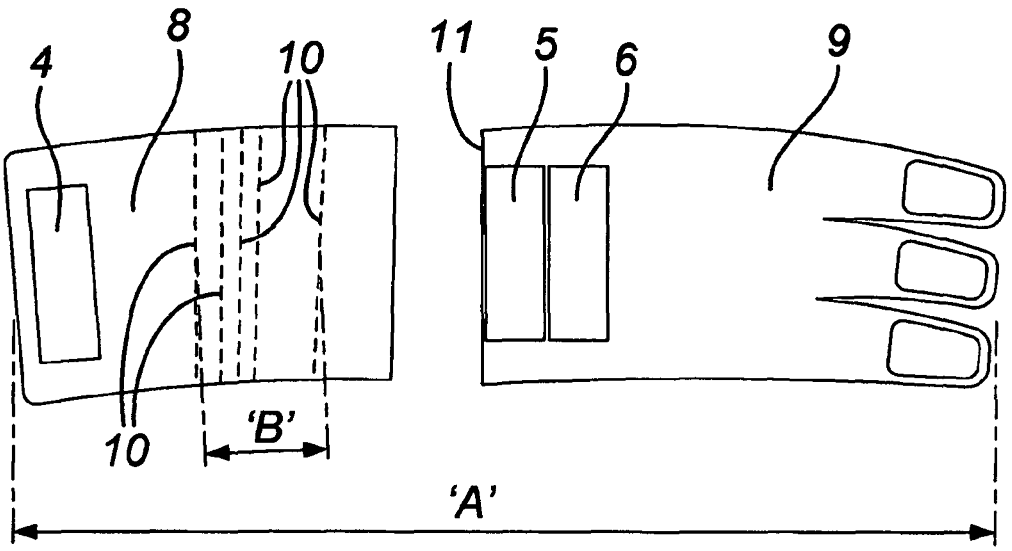
FIG. 5 is a plan view of a calf impulse therapy garment constructed in accordance with the invention.

FIG. 5 illustrates a universal sized calf garment constructed in the form of a two-piece garment comprising single bladder wrap component 8 and dual bladder wrap component 9 where the circumferential length dimension 'A' and relative separation of bladder 4 from bladders 5, 6 is adjustable according to the relative positioning of component 8 with respect to item 9. In addition, sizing indication is provided in the form of a number of marker lines 10 used in conjunction with edge reference 11.

Figure 6:
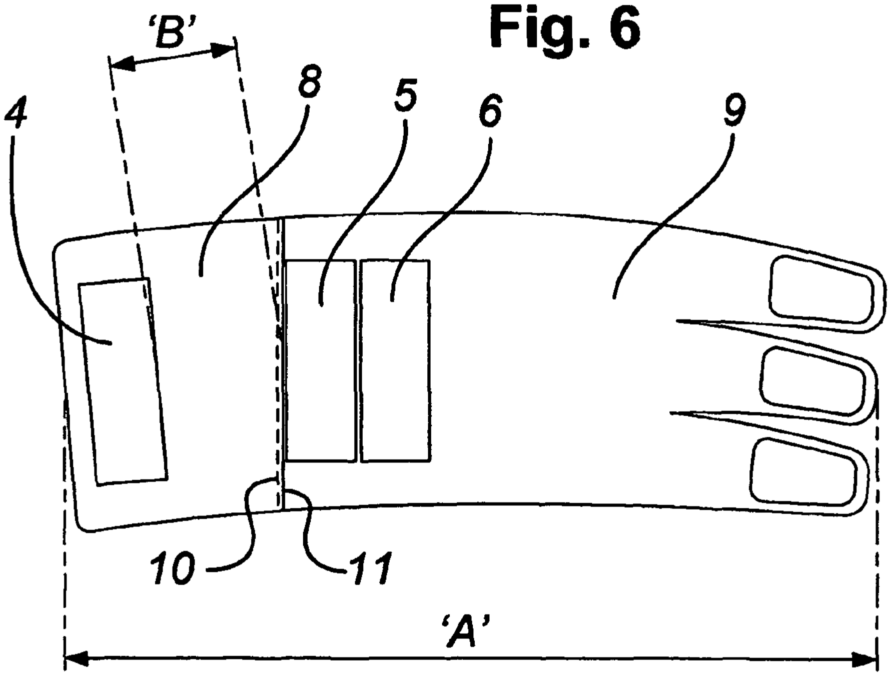
FIG. 6 is a plan view of the calf garment in FIG. 5 constructed in the form of a two-piece garment for use with a person of small physique.

FIG. 6 shows a universal sized calf garment similar to FIG. 5 and constructed in the form of a two-piece garment where the dimension 'A' relates to a calf of minimal circumference as might be evident to a person of smaller physique. In addition, dimension 'B' correspondingly relates to separation of single bladder 4 from dual bladders 5, 6. The example as shown is an assembly of the two-piece individual components 8, 9 to effectively form a one-piece garment by alignment of closest marker line 10 with edge 11 where for reference only, dimension 'A' is of the order of 50 cm and dimension 'B' 8 cm.

Figure 7:
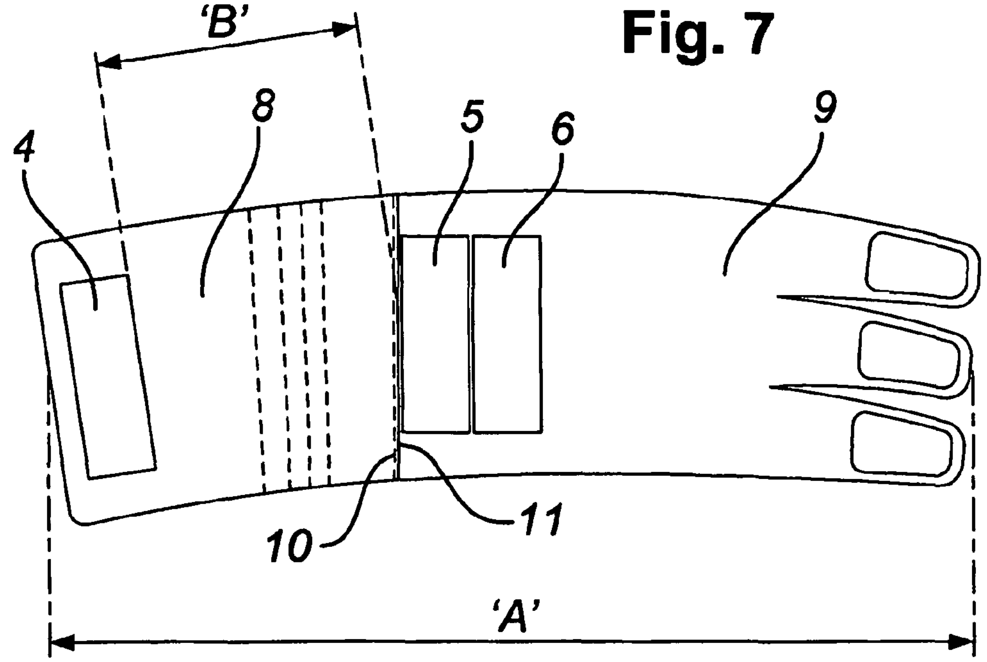
FIG. 7 is a plan view of the calf garment of FIG. 5 for use with a person of larger physique.

FIG. 7 shows a universal sized calf garment similar to FIGS. 5 and 6 constructed in the form of a two-piece garment where the dimension 'A' relates to a calf of maximal circumference as might be evident to a person of larger physique. In addition, dimension 'B' correspondingly relates to separation of single bladder 4 from dual bladders 5, 6. The example as shown is an assembly of the two piece individual components 8, 9 to effectively form a one-piece garment by alignment of farthest marker line 10 with edge 11 where for reference only, dimension 'A' is of the order of 60 cm and dimension 'B' 17 cm.

Figure 8:
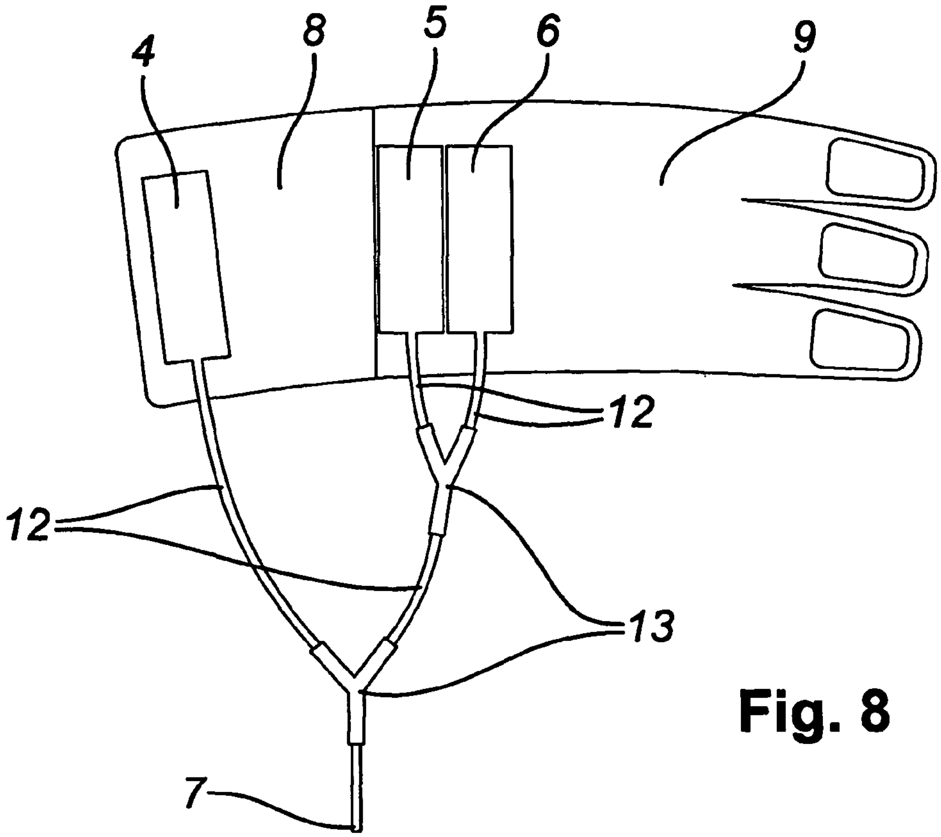
FIG. 8 is a plan view of the garment of FIG. 1 or 5 illustrating a method of interconnection between bladder elements in the garment and an external fluid source.

FIG. 8 shows an impulse therapy calf garment constructed in the form of either a single or as shown, a combined two-piece garment incorporating a method of interconnection between bladder elements and an external fluid source.

Assembled wrap components 8, 9, incorporate a single bladder 4 and dual bladders 5, 6 each having an attached conduit 12 for admission and exhaustion of fluid to inflate and deflate the bladders. For convenience the conduits 12, may be terminated in branched connectors 13, so that a single conduit or hose 7 can be attached to an external source of fluid such as an A-V Impulse System® controller, to control the filling, pressurisation and venting functions.

FIG. 9 is a plan view of a calf garment constructed in the form of a two-piece garment comprising single bladder wrap component 8 and dual bladder wrap component 9 but with an alternative method of interconnection between bladder elements.

Single bladder wrap component 8 incorporates bladder 4 having an integrated interconnecting conduit 14 traversing from bladder 4 to mating zone 15.

Interconnecting conduit 14 comprises fluid passages 16 and interspaced boundaries 17 formed, for example, by RF welding 2 layers of polymer film. The illustration shows five such fluid passages 16, but either a single or multiple passages are permissible. The technique of employing multiple fluid passages 16 and boundaries 17 is beneficial to minimise the inflated conduit volume, in comparison with the inflated bladder volume, to maximise fluid utilisation and reduce occlusion of the fluid delivery or exhaustion particularly when the garment is configured in practice in cylindrical form around the calf and the patient is supine in bed. Interconnecting conduit 14 may be constructed from the same polymer materials and process as the bladder 4.

Interconnecting conduit 14 is terminated at mating zone 15 bounded by an adhesive seal 18. The outside or backside film layer 25 of mating zone 15 is homogeneous and impervious to fluid passage whereas the inside or skin side film layer 24 is perforated, contains apertures or is otherwise porous.

Dual bladder wrap component 9 incorporates bladders 5, 6. Gallery 19 joins bladders 5, 6 so that bladder 5 is in fluidic communication with bladder 6. Bladder 6 incorporates an aperture, perforation or porosity 20 in the film outside layer and corresponds with a mating aperture 21 in wrap 9 so that fluid can enter or exhaust from the bladder to the outside of wrap 9.

Preparatory to use, the circumference of the patient's calf is measured and the relative size of the combined universal garment determined and set by combining the dual bladder wrap component 9 with the single bladder wrap component 8 according to alignment of edge reference 11 with the appropriate marker line 10.

When the single and dual wrap parts are combined aperture 20 is configured to be superimpose on mating zone 15 across the range of size adjustment, in the circumferential sense and to be tolerant of mating accuracy between the individual wrap components 8, 9 in the lateral and rotational sense. Pressure sensitive adhesive seal 18 surrounds the mating zone 15 and provides a fluid tight seal between the single and dual wrap components.

In the example shown fluid enters the assembled universal garment via conduit or hose 7 connected to bladder 4, then through fluid passages 16 of conduit 14 to mating zone 15 sealed by adhesive seal 18, apertures 21 and 20 into bladder 6 and finally through gallery 19 to bladder 5. Provided that all fluid pathways are appropriately sized bladders 5, 6 will inflate and deflate in near simultaneous approximation with bladder 4 to apply a focused and unified force to the calf.

As illustrated, adhesive seal 18 provides both a fluid tight seal and a mechanical means of joining the single and dual bladder components. In operation the joining means must be sufficiently robust to withstand the radial and circumferential forces generated from repeated inflation of the bladders to between ~40 and 200 mmHg.

FIG. 9*a* is an enlarged sectional view of the wrap 8 of FIG. 9 along section X-X of mating zone 15 showing in details fluid passages 16 and interspaced boundaries 17 in conjunction with adhesive seal 18. The mating zone is shown constructed from RF welded polymer, film skinside 24 and film outside 25. Not shown but may be added, is a spacer to be included in each fluid passage to prevent occlusion.

Figure 10:
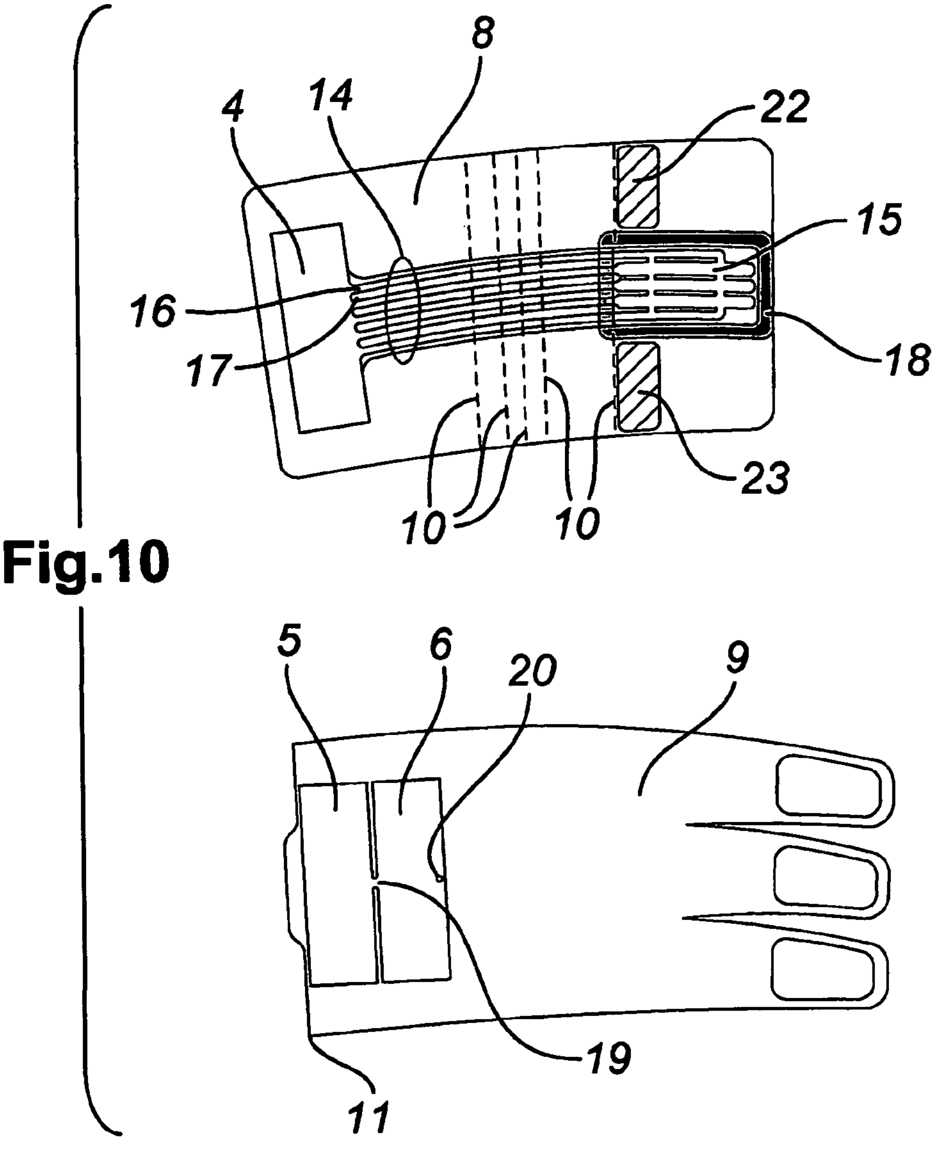
FIG. 10 is a plan view of a calf garment constructed in accordance with a further preferred embodiment of the invention.

FIG. 10 is a plan view of a universal sized calf garment constructed in the form of a two piece garment comprising single bladder wrap component 8 and dual bladder wrap component 9 having an alternative method of combining wrap component 8 to wrap component 9. Bladder 4 and integrated interconnecting conduit 14 are connected to mating zone 15 as previously. Adhesive seal 18 surrounds mating zone 15 to provide a fluid tight seal and to a degree an adhesive bond to secure wrap component 8 to wrap component 9. In addition, further bonding strength alone, is achieved through closure means upper 22 and closure means lower 23 which may take the form of one or more pressure sensitive adhesive strips or areas interfacing between the inside or skin side surface of wrap 8 and the outside of wrap 9. Alternatively, the closure means 22, 23 could take the form of the hook component of a hook and loop closure system mating with a loop material on the outside of wrap 9.

A beneficial aspect of using an adhesive closure means 22, 23 either in isolation of or in conjunction with adhesive seal 18 is that the adhesive closure system may be selected to allow single, minimal or multiple re-applications of wrap 8 to wrap 9 as disclosed in International Application PCT/GB2006/002674 owned by the present applicant, either as a means of limiting, tolerating or facilitating re-use.

Figure 11:
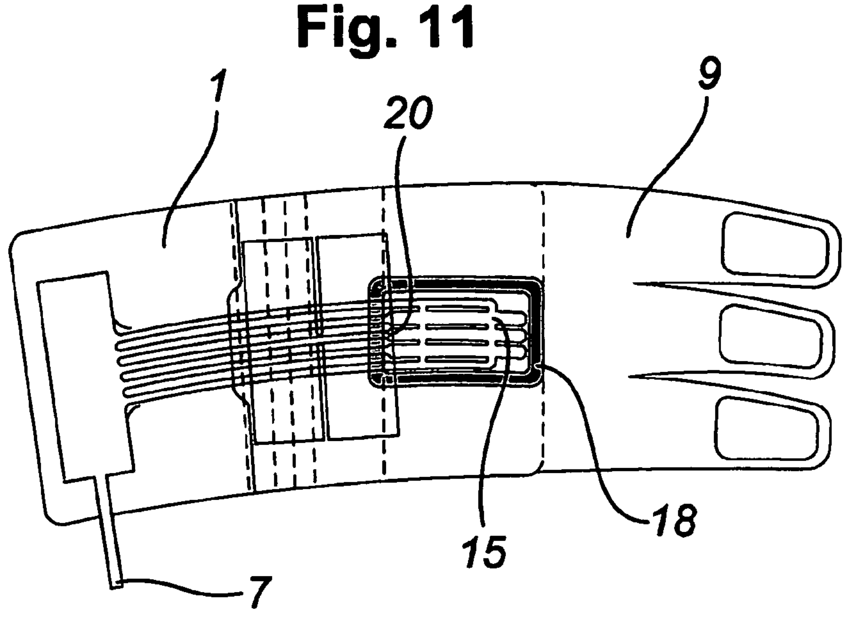
FIG. 11 is a plan view of a two-piece universal calf garment incorporating a method of fluid conduit interconnection adjusted to suit a small sized calf.

FIG. 11 is a plan view of a two-piece universal garment with integrated fluid conduit adjusted to suit a small size calf. In this illustration single bladder wrap component 8 is joined to dual bladder wrap component 9 so that aperture 20 and mating aperture 21 are aligned with the left hand side of mating zone 15. Adhesive seal 18 provides a fluid tight seal and mechanical retention of wrap 8 to wrap 9. Fluid introduced at hose 7 will therefore inflate both the single and dual bladder elements of the universal garment adjusted for small physique or conversely allow the inflation system to be vented.

Figure 12:
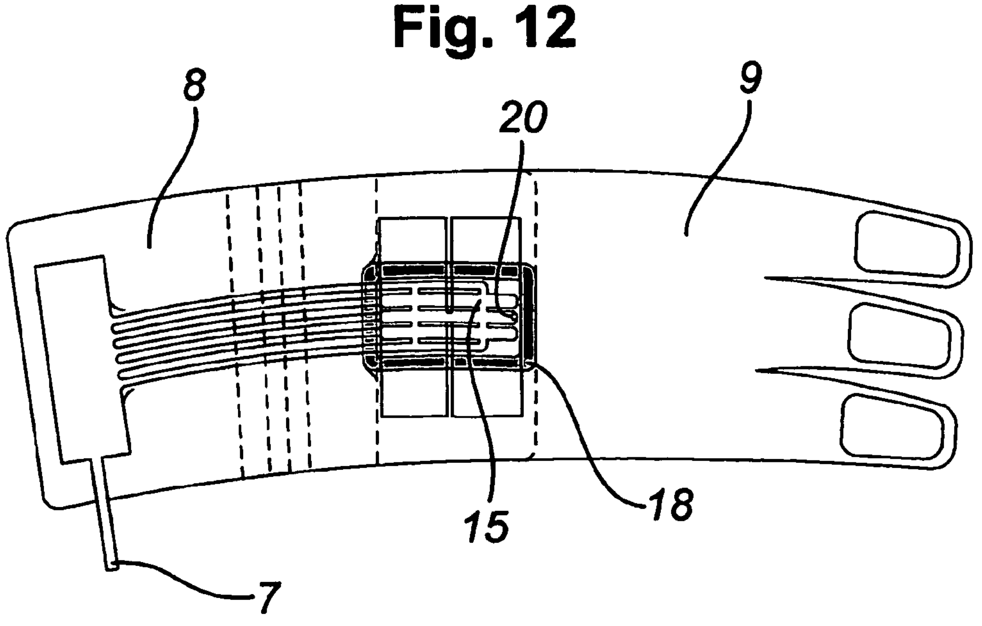
FIG. 12 is a plan view of a two-piece universal calf garment similar to FIG. 11 but for use with a large sized calf.

FIG. 12 is a plan view of a two-piece universal calf garment with integrated fluid conduit adjusted to suit a large size calf. In this illustration single bladder wrap component 8 is joined to dual bladder wrap component 9 so that aperture 20 and mating feature 21 are aligned with the right hand side of mating zone 15. Adhesive seal 18 provides a fluid tight seal and mechanical retention of wrap 8 to wrap 9. Fluid introduced at hose 7 will therefore inflate both the single and dual bladder elements of the universal garment adjusted for large physique or conversely allow the inflation system to be vented.

Clearly, all intermediate physiques covering the range from small to large can be accommodated by appropriate adjustment of wrap 8 with respect to wrap 9 without detriment to flow in all system components.

Embodiments of the invention as described hereinbefore may be summarised as follows:

1. A means of configuring a universal size garment for inflation of the calf.
2. A means of adjustment of a universal garment to comply with a range of calf sizes.
3. A means of indicating the alignment of a two-piece garment to define the circumferential size of the assembled garment.
4. A means of indicating the alignment of a two-piece garment to define the relative locations of the single bladder to dual bladder components of the assembled garment.
5. A means of configuring a fluid connection to an inflatable garment with more than one inflatable bladder.
6. A means of distribution of fluid between separate cells of an inflatable device.
7. A means of distribution of fluid between separate cells of an inflatable device that is adjustable in size.
8. A means of providing a pressure seal between component parts of a garment with a plurality of components.
9. A means of providing a pressure seal between component parts where circumferential adjustment is permissible.
10. A means of providing a pressure seal between component parts where lateral adjustment is permissible.
11. A means of providing a pressure seal between component parts where axial or rotational misalignment is tolerated.

12. A means of combining a pressure seal with a joining means in a two-piece garment.
13. A means of providing an additional joining method independent of a pressure seal.
14. A means of defining quantitative readjustment of the two parts of a garment by selection of an appropriate joining method.

The invention claimed is:

1. An inflatable medical garment for applying to parts of the body such as the foot, calf and hand to enhance blood circulation in the body part, the garment comprising:

a circumferential wrap having a first section and a second section separate from said first section, each wrap section being provided with one or more inflatable bladders, the bladders on each wrap section being fluidly connected by fluid delivery passages formed on the respective wrap section, the passages including a coupling in an engagement zone for connecting said passages to each other so the bladders of each wrap section simultaneously inflate the bladders of the corresponding wrap section from a single source, said coupling includes a mating area in the engagement zone that mates with the coupling of the other wrap section to form a continuous path for fluid communication between bladders on both wrap sections, the fluid delivery passage formed on said first wrap section providing communication between said bladders thereon and said mating area, said mating area providing a fluid access to said first delivery passage that communicates with a fluid access to said second delivery passage having a smaller cross-sectional area than said fluid access to the first passage such that fluid communication is maintained between the bladders on each wrap section as the fluid access to the second passage moves to different parts of the mating area during selective engagement of the wrap sections in the engagement zone, a closure for securing the wrap around the body part such that upon cyclic inflation of the bladders a cyclical pressure is applied to the body part to circulate blood in the body and a fastener on at least one of the first section and the second section for selectively joining the first section to predetermined locations of the second section for adjusting the size of the garment to fit body parts of differing shape and size.

2. A garment as claimed in claim 1 in the form of an inflatable wrap for application to the calf of a leg, the fastener permits the position of engagement of the first wrap section to be adjusted relative to the second wrap section to permit a selected length of wrap to be applied around the leg in accordance with calf size.

3. A garment as claimed in claim 2 wherein the first wrap section is provided with said engagement zone, the zone being provided with spaced indication markers to which a leading edge portion of the second wrap section is selectively aligned in accordance with the required circumferential length of the wrap.

4. A garment as claimed in claim 3 wherein two inflatable bladders are incorporated in at least one of said first and second wrap sections such as to provide selective application of the bladders to chosen areas of the calf.

5. A garment as claimed in claim 4 including branched tube connections for supplying pressurized fluid from a single source to said bladders.

6. A garment as claimed in claim 1 wherein the mating area is bounded by adhesive for sealable engagement with the second wrap section to prevent fluid escape from the mating area.

7. A garment as claimed in claim 6 wherein there is provided one or more pressure sensitive adhesive strips for interfacing between the two wrap sections in the engagement zone thereby to secure the two wrap sections together.

* * * * *